United States Patent
Takano

(10) Patent No.: US 11,160,533 B2
(45) Date of Patent: Nov. 2, 2021

(54) ULTRASOUND IMAGE PICKUP APPARATUS

(71) Applicant: Hitachi, Ltd., Tokyo (JP)

(72) Inventor: Shinta Takano, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1549 days.

(21) Appl. No.: 14/910,358

(22) PCT Filed: Jul. 17, 2014

(86) PCT No.: PCT/JP2014/069116
§ 371 (c)(1),
(2) Date: Feb. 5, 2016

(87) PCT Pub. No.: WO2015/025655
PCT Pub. Date: Feb. 26, 2015

(65) Prior Publication Data
US 2016/0174938 A1    Jun. 23, 2016

(30) Foreign Application Priority Data
Aug. 21, 2013    (JP) .............................. JP2013-171584

(51) Int. Cl.
*A61B 8/00*    (2006.01)
*A61B 8/08*    (2006.01)
(Continued)

(52) U.S. Cl.
CPC .............. *A61B 8/4488* (2013.01); *A61B 8/14* (2013.01); *A61B 8/5269* (2013.01);
(Continued)

(58) Field of Classification Search
None
See application file for complete search history.

(56) References Cited

U.S. PATENT DOCUMENTS

| | | | |
|---|---|---|---|
| 8,485,977 B2 | 7/2013 | Hirama | |
| 2009/0326377 A1* | 12/2009 | Hirama | .............. G01S 7/52046 600/447 |
| 2010/0056917 A1* | 3/2010 | Karasawa | ............ A61B 8/0833 600/443 |

FOREIGN PATENT DOCUMENTS

| | | |
|---|---|---|
| CN | 101548896 A | 10/2009 |
| JP | 10-277042 A | 10/1998 |
| JP | 2009-240700 A | 10/2009 |

OTHER PUBLICATIONS

International Preliminary Report on Patentability received in corresponding International Application No. PCT/JP2014/069116 dated Mar. 3, 2016.

(Continued)

*Primary Examiner* — Katherine L Fernandez
*Assistant Examiner* — Michael S Kellogg
(74) *Attorney, Agent, or Firm* — Mattingly & Malur, PC

(57) ABSTRACT

A transmitting beamformer performs convergence transmission that forms a transmission focus of an ultrasonic beam in a subject. A receiving beamformer comprises a virtual sound source method-based delay amount calculation part that obtains delay amount of a received signal with regarding the transmission focus as a virtual sound source, and a correction operation part that corrects the delay amount obtained by the virtual sound source method-based delay amount calculation part depending on position of imaging point. Delay amounts can be thereby obtained with good accuracy for imaging points in a wide area.

6 Claims, 17 Drawing Sheets

(51) Int. Cl.
  *G01S 7/52*    (2006.01)
  *A61B 8/14*    (2006.01)
  *G01S 15/89*   (2006.01)
(52) U.S. Cl.
  CPC ...... *G01S 7/52019* (2013.01); *G01S 7/52046* (2013.01); *G01S 15/8915* (2013.01); *G01S 15/8997* (2013.01); *G01S 15/8906* (2013.01)

(56) References Cited

OTHER PUBLICATIONS

Chinese Office Action received in corresponding Chinese Application No. 201480045635.1 dated Jul. 3, 2017.
International Search Report of PCT/JP2014/069116.

* cited by examiner $$D_2 = \frac{D_1 |\cos\theta|}{\cos\theta_1}$$

ULTRASOUND IMAGE PICKUP APPARATUS

TECHNICAL FIELD

The present invention relates to an ultrasonic imaging technique for imaging an internal structure in a subject, in which a probe is applied to the subject, ultrasonic waves are transmitted through it, and ultrasonic waves reflected in the subject are received and used for imaging.

BACKGROUND ART

Ultrasonic imaging technique is a technique for non-invasively imaging inside of a subject including human body by using ultrasonic waves (sonic waves not intended to be heard, generally sonic waves of high frequencies of 20 kHz or higher). For example, ultrasonic imaging apparatuses for medical use transmit ultrasonic beams to the inside of the body of subject through an ultrasound probe, and receives echo signals from the inside of the body. The received signals are subjected to a phasing processing with a receiving beamformer, and used by an image processing part to generate an ultrasonogram.

There are two kinds of methods for transmitting ultrasonic beams from an ultrasound probe to a subject, that is, expansion transmission that transmits ultrasonic beams spreading in a fan shape, and convergence transmission that converges ultrasonic beams at a transmission focus provided in a subject. Since the convergence transmission provides high transmission sound pressure, it is suitable for a method of imaging harmonic components (tissue harmonic imaging, THI), etc. By using the THI imaging, artifacts generated by side lobe or repeated reflection are reduced, and contrast is improved.

For the convergence transmission, there is frequently used the virtual sound source method, in which receiving beamforming is performed by regarding the focus as sound source. However, the virtual sound source method suffers from a problem that delay amount cannot be accurately obtained in the neighborhood of the transmission focus. Patent document 1 discloses a technique of aperture synthesis using an improved virtual sound source method in the ultrasonic imaging in which convergence transmission is performed. Specifically, in a region in which energy of ultrasonic beams converges on the focus (region A shown in FIG. 2 of Patent document 1), aperture synthesis is performed with regarding the focus as a virtual sound source, and in the surrounding regions (regions B and C) in which ultrasonic energy diffuses, aperture synthesis is performed with regarding that spherical waves are emitted from the end of the probe. Patent document 1 also describes that the aperture synthesis is not performed in side lobe regions further outside the regions B and C (regions D and E shown in FIG. 6 of Patent document 1).

PRIOR ART REFERENCES

Patent Document

Patent document 1: Japanese Patent Unexamined Publication (KOKAI) No. 10-277042

SUMMARY OF THE INVENTION

Object to be Achieved by the Invention

All the aforementioned regions A, B, and C for which delay amount is obtained in the technique of Patent document 1 are regions within the main lobe, and information of the area outside the regions irradiated with the side lobe is not used. Therefore, the area for which information is obtained is narrow, and it is difficult to realize high-speed imaging.

Hereafter, the reason why delay amount cannot be accurately obtained by the virtual sound source method in the neighborhood of the transmission focus will be explained with reference to FIG. 1. In order to obtain delay amount by the virtual sound source method, acoustic velocity and sonic wave propagation time in the subject are required. The sonic wave propagation time is divided into the outward propagation time from the start trigger of sonic wave transmission to a certain imaging point, and the return propagation time from the certain imaging point to each element of the probe array. In order to obtain the outward propagation time for the imaging point 200 shown in FIG. 1, propagation time from the transmission caliber center point 202 to the transmission focus 203 is obtained first, and from this propagation time, propagation time from the transmission focus 203 to the imaging point 200 is subtracted. In order to obtain the outward propagation time for the imaging point 201, propagation time from the transmission caliber center point 202 to the transmission focus 203 is obtained first, and to this propagation time, propagation time from the transmission focus 203 to the imaging point 201 is added. Which one of subtraction and addition is performed is determined depending on whether the imaging point is on the side of the probe array 100 with respect to the transmission focus 203, and when the imaging point locates on the side of the probe array 100, the subtraction is performed, whereas when the imaging point locates on the other side, the addition is performed.

Circles 204 and 205 passing the imaging point 200, of which center is the transmission focus 203, each represent a same phase surface, and the outward propagation times of all the imaging points on these circles 204 and 205 have the same value. In FIG. 1, the crossing broken lines 206 are lines geometrically connecting the both ends of the line of a plurality of elements in the probe array 100 and the transmission focus 203 (transmitted sonic wave end 206), and indicate the irradiation range of the transmitted beams defined without taking diffraction and diffusion of ultrasonic beams into consideration. When the imaging point locates in the region between the transmitted sonic wave ends 206, delay amount may be obtained with good accuracy by the virtual sound source method.

However, if there are supposed imaging points locating outside the region between the transmitted sonic wave ends 206, and on the surface of the same phase, such as imaging points 300 and 301 shown in FIG. 2, actual outward propagation times for them are not substantially different, but since the imaging point 300 is on the side where it is closer to the probe array 100 compared with the transmission focus 203, and the imaging point 301 is on the side where it is remoter from the probe array 100 compared with the transmission focus 203, the delay amounts obtained for them by the virtual sound source method should be significantly different. That is, the outward propagation time for the imaging point 300 is calculated by subtracting the propagation time from the transmission focus 203 to the imaging point 300 from the propagation time from the transmission caliber center point to the transmission focus 203, whereas the outward propagation time for the imaging point 301 is calculated by adding the propagation time from the transmission focus 203 to the imaging point 301 to the propagation time from the transmission caliber center point to the transmission focus 203. Therefore, the outward propagation times for them should significantly differ. Further, although the actual outward propagation times for the imaging point 300 and the imaging point 302 differ, they are calculated to be the same value when they are calculated by using the virtual sound source method. The same shall apply to the imaging point 301 and the imaging point 303.

As described above, by the virtual sound source method, the sonic wave propagation time is not correctly calculated for an imaging point locating near the transmission focus, and outside the region between the transmitted sonic wave ends 206, and therefore accuracy of the delay amount calculation is degraded.

The present invention solves the aforementioned problem, and an object of the present invention is to provide an ultrasonic imaging apparatus that highly accurately obtains delay amount for imaging points in a large area even when the convergence transmission is performed.

Means for Achieving the Object

In order to achieve the aforementioned object, the ultrasonic imaging apparatus of the present invention comprises an ultrasonic element array in which a plurality of ultrasonic elements are arranged along a predetermined direction, a transmitting beamformer that forms an ultrasonic beam that is transmitted into a subject by the ultrasonic element array, a receiving beamformer that performs phasing of a plurality of received signals obtained by receiving the ultrasonic waves reflected in the subject with the ultrasonic element array by delaying them, and an image processing part that generates image data by using results outputted by the receiving beamformer. The transmitting beamformer performs convergence transmission, which forms a transmission focus of ultrasonic beams in the subject. The receiving beamformer comprises a virtual sound source method-based delay amount calculation part that obtains delay amount of a received signal with regarding the transmission focus as a virtual sound source, and a correction operation part that corrects the delay amount obtained by the virtual sound source method-based delay amount calculation part depending on position of imaging point.

Effect of the Invention

With the ultrasonic imaging apparatus of the present invention, delay amount obtained by the virtual sound source method is corrected, and therefore highly accurate delay amount is obtained for imaging points in a wide area even when the convergence transmission is performed. Accordingly, a highly precise ultrasonogram is obtained.

BRIEF DESCRIPTION OF THE DRAWINGS

FIG. 15, (b) is an explanatory drawing showing the phasing area 105b of the ultrasonic diagnostic apparatus of the fifth embodiment.

FIG. 16, (b) is an explanatory drawing showing the image generation area 501 in the case of high-speed imaging performed with the conventional phasing area 105a. FIG. 16, (c) is an explanatory drawing showing the phasing area 105b and the image generation area 501 of the fifth embodiment.

MODES FOR CARRYING OUT THE INVENTION

Hereafter, embodiments of the present invention will be explained with reference to the drawings. However, the present invention is not limited to the following embodiments.

First Embodiment

Figure 3:
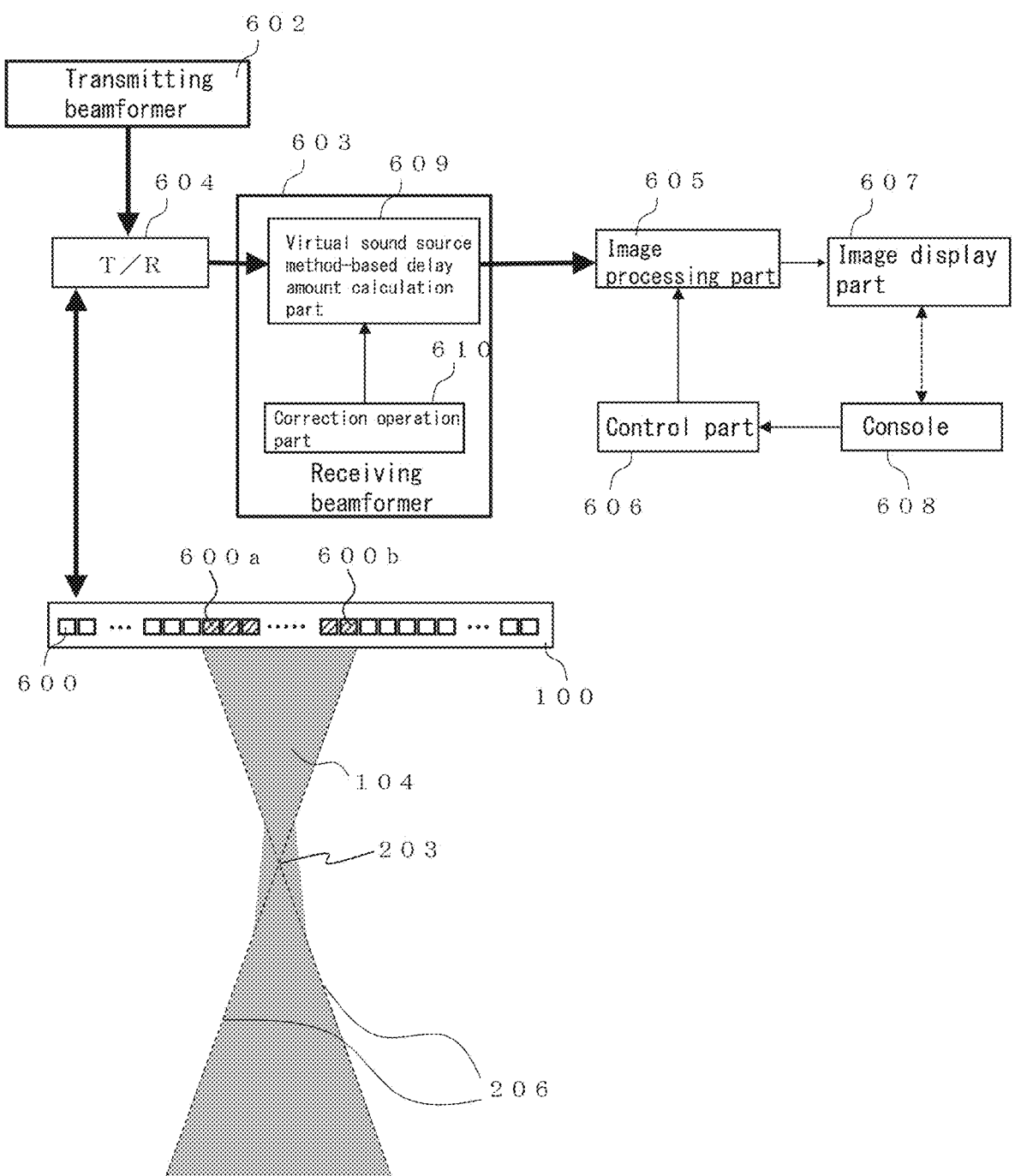
FIG. 3 is a block diagram showing the configuration of the ultrasonic diagnostic apparatus of the first embodiment.

The ultrasonic imaging apparatus of the first embodiment of the present invention comprises, as shown in FIG. 3, for example, an ultrasonic element array (probe array) 100 in which a plurality of ultrasonic elements 600 are arranged along a predetermined direction, a transmitting beamformer 602, a receiving beamformer 603, and an image processing part 605. The transmitting beamformer 602 forms an ultrasonic beam 104 to be transmitted into a subject by the ultrasonic element array 100. The receiving beamformer 603 performs phasing of a plurality of received signals obtained by receiving ultrasonic waves reflected within the subject by the ultrasonic element array 100 by delaying them. The image processing part 605 generates image data using results outputted by the receiving beamformer 603.

The transmitting beamformer 602 performs convergence transmission that forms the transmission focus 203 of the ultrasonic beam 104 in the subject. The receiving beamformer 603 comprises a virtual sound source method-based delay amount calculation part 609 that obtains delay amount of a received signal with regarding the transmission focus 203 as a virtual sound source, and a correction operation part 610 that corrects the delay amount obtained by the virtual sound source method-based delay amount calculation part 609 depending on position of imaging point.

For example, when an imaging point locates outside the region between transmitted sonic wave ends 206, which are two lines connecting end ultrasonic elements 600a and 600b at the both ends among ultrasonic elements 600 that transmit the ultrasonic beam 104 into the subject, and the transmission focus 203, respectively (for example, imaging point 802 shown in FIG. 4), the correction operation part 610 corrects the delay amount ($D_1$) obtained by the virtual sound source method-based delay amount calculation part 609 for the imaging point 802.

Figure 4:
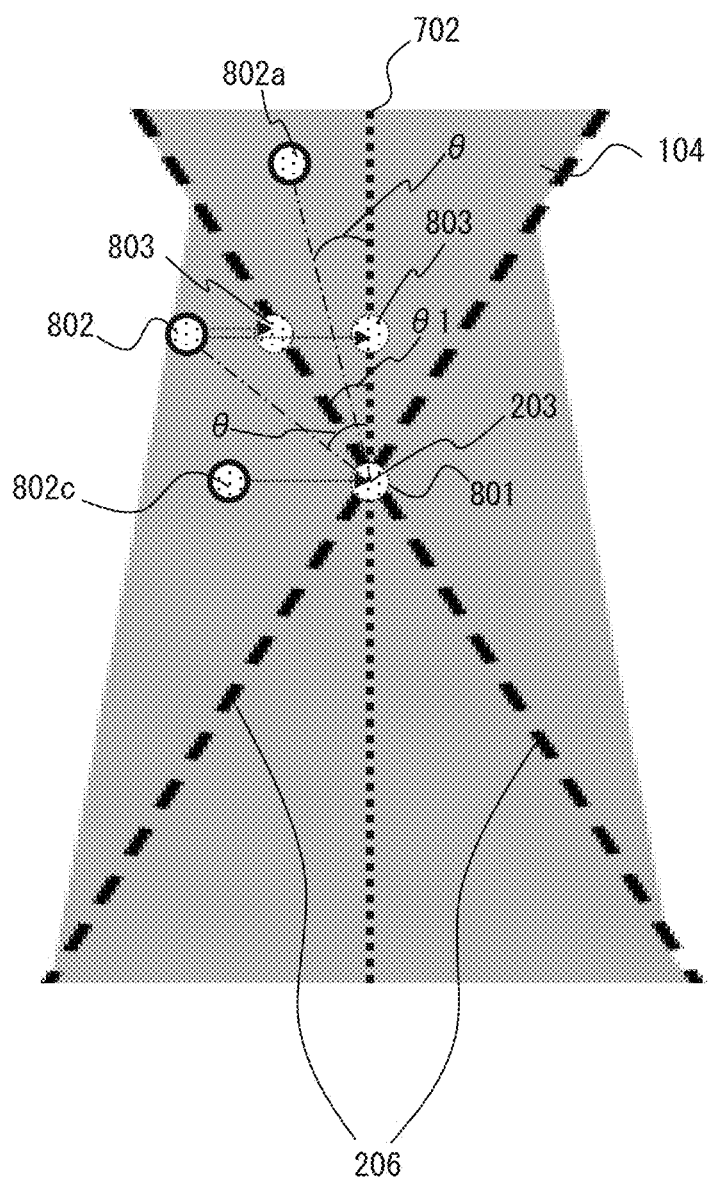
FIG. 4 is a drawing for explaining the principle of obtaining corrected delay amount in the first embodiment.

Specifically, as shown in FIG. 4, when the imaging point 802 locates outside the transmitted sonic wave end 206, the correction operation part 610 corrects the delay amount ($D_1$) obtained by the virtual sound source method-based delay amount calculation part 609 for the imaging point 802 using the delay amount ($D_2$) obtained for the point 803 according to the virtual sound source method.

The point 803 is a point locating on the line of the transmitted sonic wave end 206 or between two of the transmitted sonic wave ends 206. The point 803 is preferably a point obtained by projecting the imaging point 802 on the nearest transmitted sonic wave end 206, because such a point reduces calculation complexity. The imaging point 802 is projected on the transmitted sonic wave end 206 by, for example, moving the imaging point 802 along the direction perpendicular to the sound axis 702 of the ultrasonic beam 104.

Figure 5:
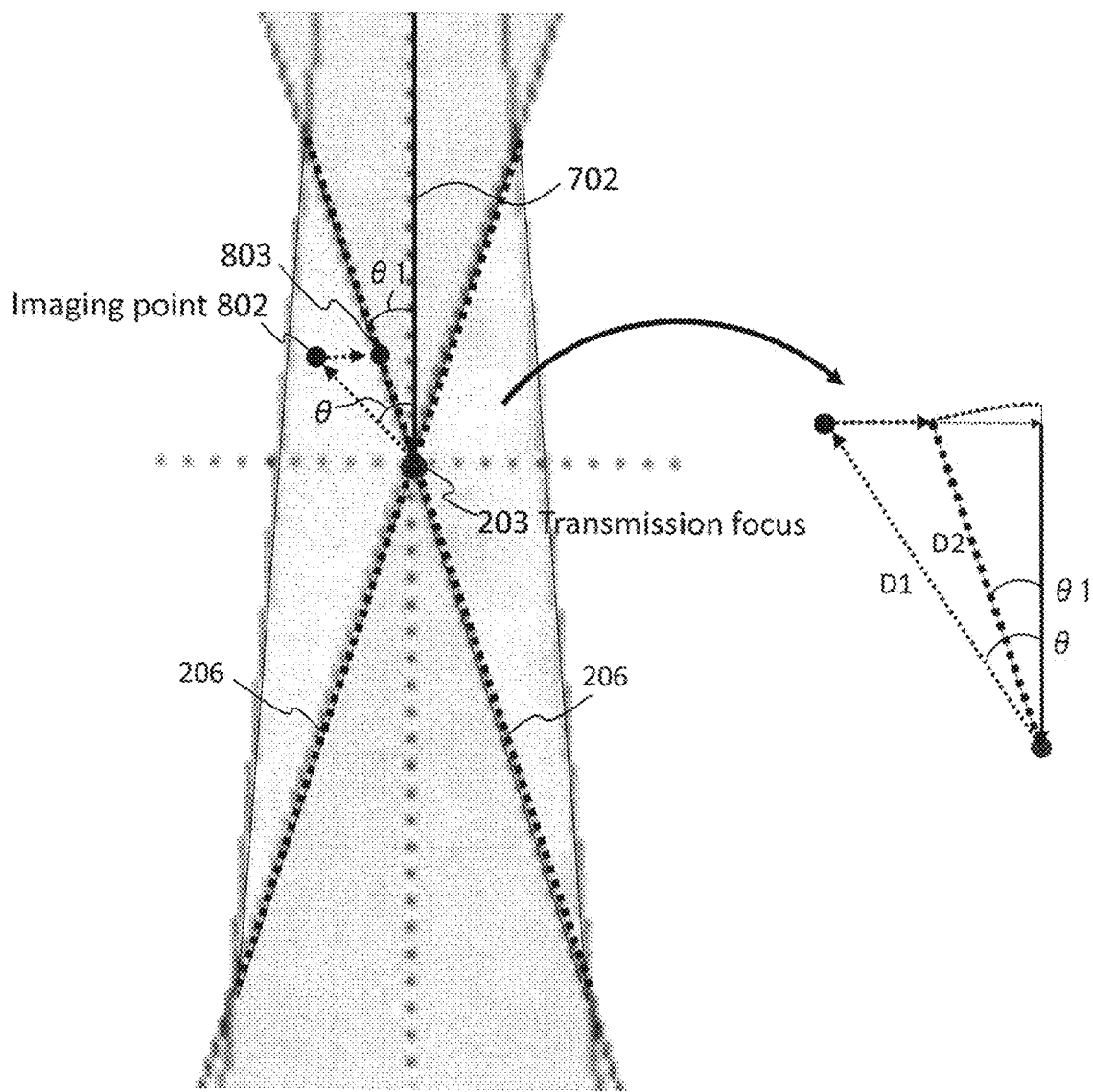
FIG. 5 is a drawing for explaining the equation for obtaining delay amount ($D_2$) for a point 803 of the first embodiment.

The correction operation part 610 obtains a corrected delay amount D by, for example, weighting the aforementioned delay amount ($D_1$) and the delay amount ($D_2$), and adding them. For obtaining weight values for the weighting, there is used, for example, a function of the angle θ formed by the line connecting the imaging point 802 and the transmission focus 203, and the sound axis 702 of the ultrasonic beam 104 as a variable (FIG. 5).

Hereafter, still more specific explanation will be made. As shown in FIG. 3, between the transmitting beamformer 602 and the receiving beamformer 603, and the ultrasonic element array 100, a transmission/reception separation circuit (T/R) 604 that separates transmission and reception signals is disposed. To the image processing part 605, a control part 606 that controls the image processing part 605, and an image display part 607 that displays image data are connected. To the control part 606, a console 608 for setting imaging conditions, image generation conditions etc. is connected.

Figure 1:
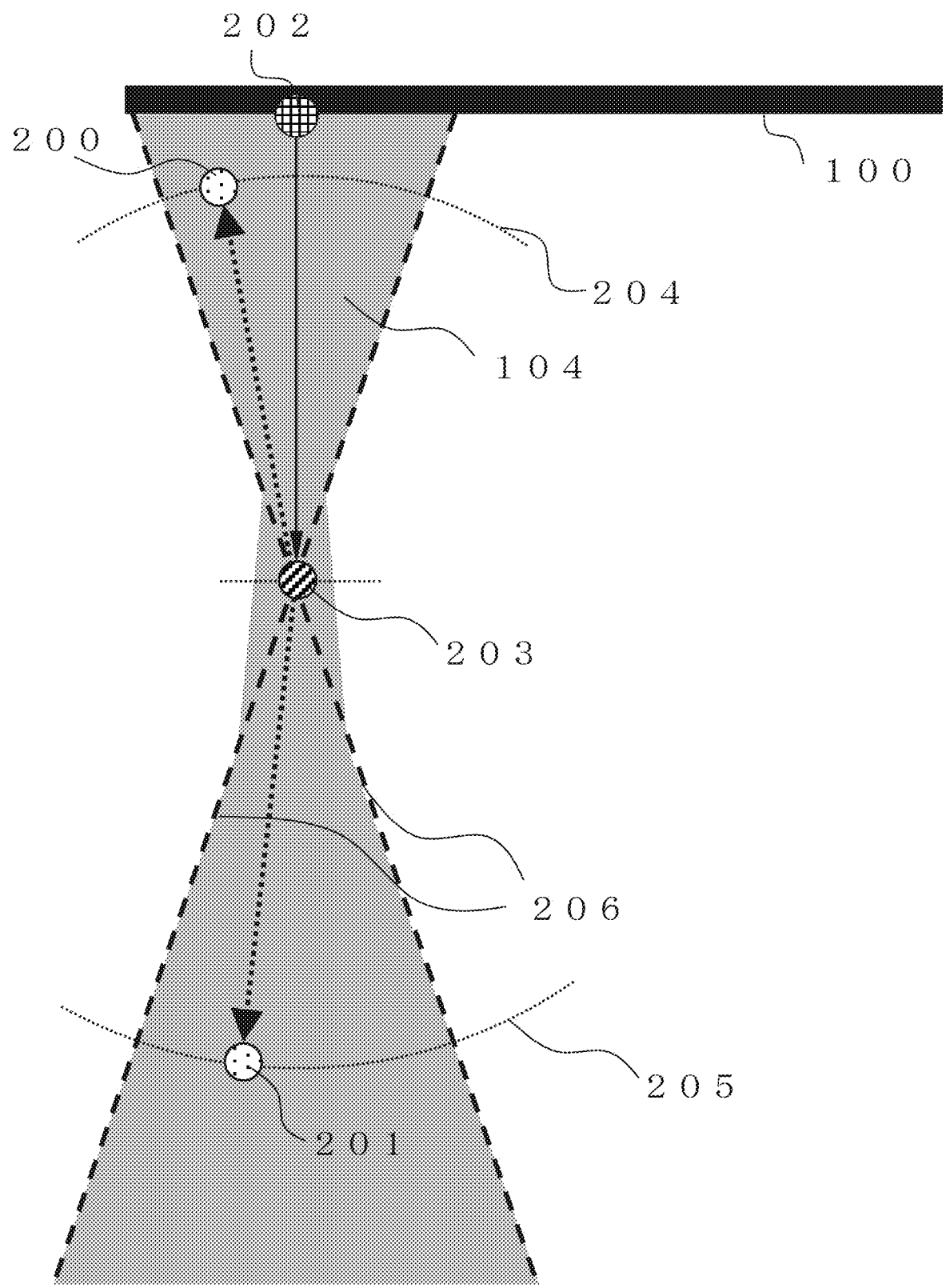
FIG. 1 is a drawing for explaining the outline of the delay amount calculation based on the virtual sound source method.
Figure 2:
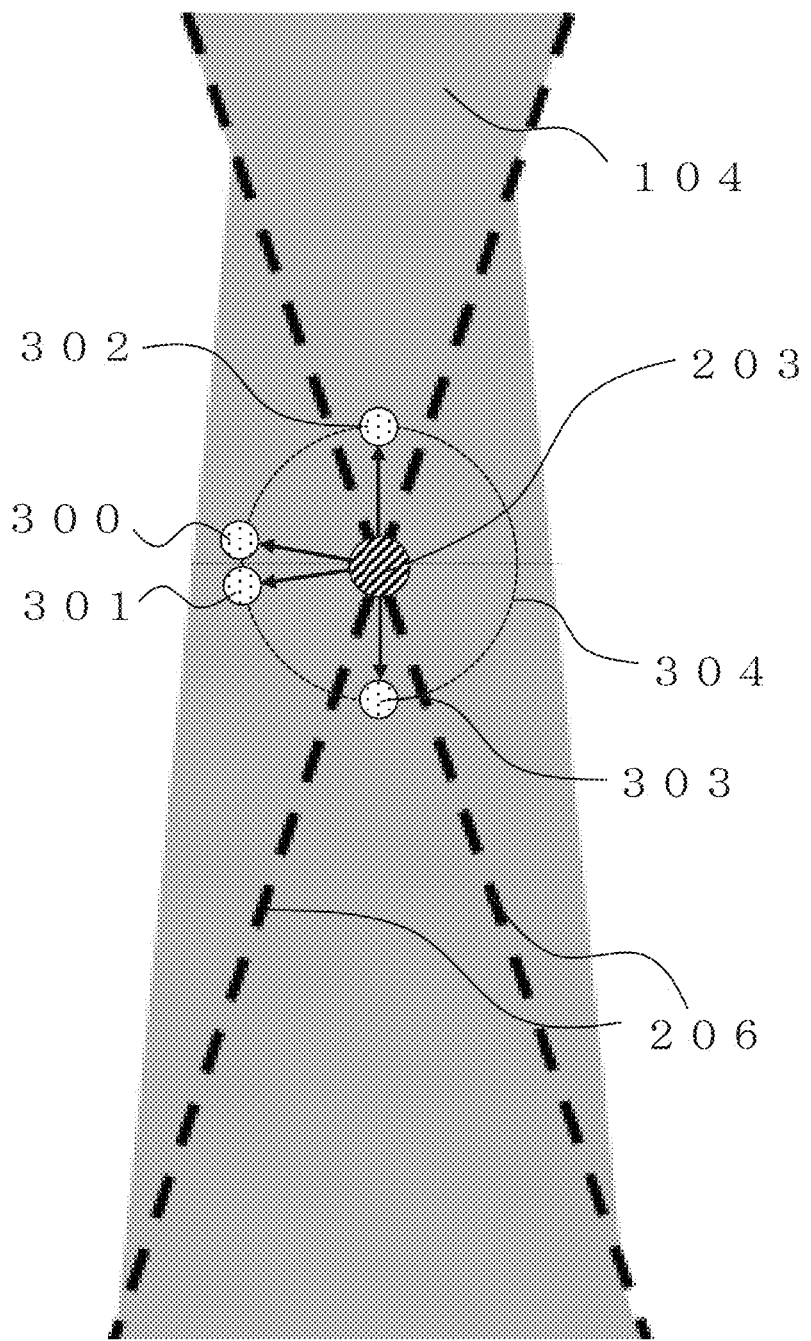
FIG. 2 is a drawing for explaining the problem of the virtual sound source method occurring at a position near the transmission focus.

The virtual sound source method-based delay amount calculation part 609 obtains delay amount ($D_1$) of a received signal by the virtual sound source method according to the distance of a desired imaging point from the transmission focus 203 with supposing that the virtual sound source locates at the transmission focus 203. Since the calculation method of the delay amount according to the virtual sound source method is a widely known method, detailed explanation thereof is omitted in this specification. But as explained with reference to FIG. 1, the delay amount is calculated by using the acoustic velocity and the sonic wave propagation time in the subject. The sonic wave propagation time is divided into the outward propagation time from the transmission start trigger of the ultrasonic beam 104 in the transmitting beamformer 602 to the imaging point, and the return propagation time from the imaging point to the ultrasonic element 600 of the ultrasonic element array 100. In order to obtain the outward propagation time, when the imaging point is on the side of the ultrasonic element array 100 with respect to the transmission focus 203 (for example, in the case of the imaging point 200 shown in FIG. 1), the propagation time from the transmission focus 203 to the imaging point 200 is subtracted from the propagation time from the transmission caliber center point 202 to the transmission focus 203. When the imaging point is at a position remoter from the ultrasonic element array 100 compared with the transmission focus 203 (for example, in the case of the imaging point 201), the outward propagation time is obtained by adding the propagation time from the transmission focus 203 to the imaging point 201 to the propagation time from the transmission caliber center point 202 to the transmission focus 203. As described above, according to the virtual sound source method, the outward propagation time is determined according to the distance from the transmission focus 203, and the circle 204 as a concentric circle, of which center is at the transmission focus 203, represents the same phase surface (wave face of transmitted sonic waves).

Figure 6:
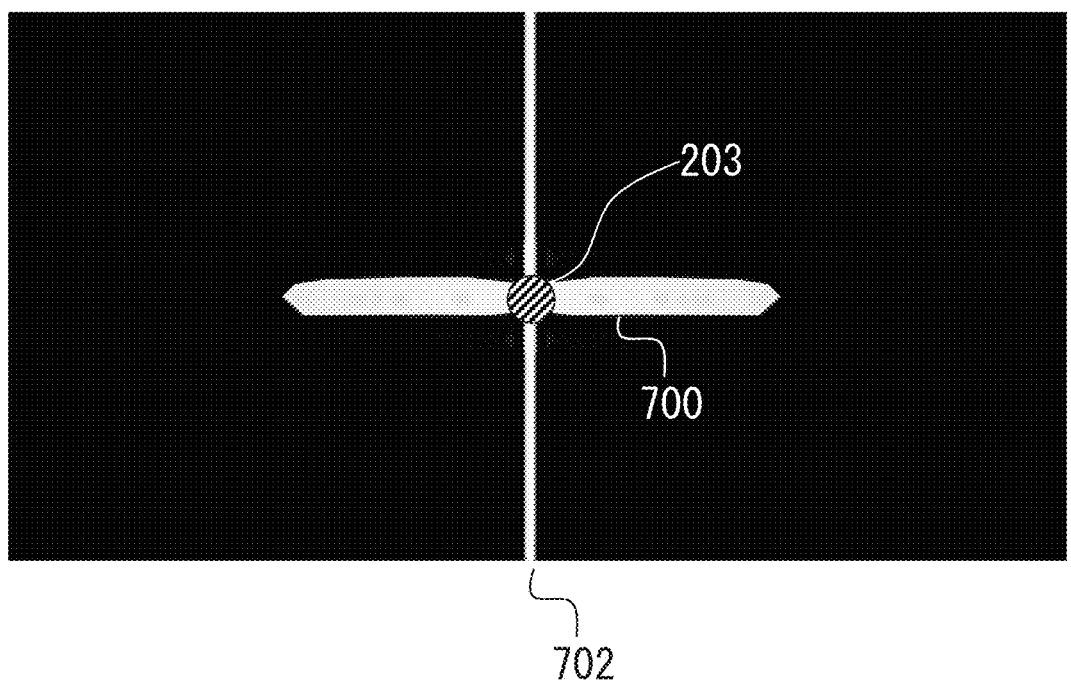
FIG. 6 is an explanatory drawing showing the shape of the wave face of the transmitted sonic waves at the depth of the transmission focus.

However, if the actual wave face of transmitted sonic waves is obtained by simulation, the wave face 700 of transmitted sonic waves is substantially perpendicular to the transmission sound axis 702 around the transmission focus 203, as shown in FIG. 6. In other words, it is substantially parallel to the surface of the ultrasonic element array 100 (in FIG. 6, the wave face of transmitted sonic waves 700 is indicated as a region of sound intensities larger than a certain value, and therefore the wave face 700 has a width for the direction of the transmission sound axis). From the above simulation result, it is estimated that the actual wave face of transmitted sonic waves does not have a shape of concentric circle having the center at the transmission focus 203, but the curvature thereof becomes smaller at a position closer to the transmission focus 203, and the wave face is substantially a straight line at the transmission focus 203. Therefore, the delay amount cannot be accurately obtained by the virtual sound source method in the neighborhood of the transmission focus 203.

Therefore, in this embodiment, the correction operation part 610 obtains a delay amount (D) by correcting the delay amount ($D_1$) obtained by the virtual sound source method-based delay amount calculation part 609 for a desired imaging point. The delay amount (D) for an imaging point in the neighborhood of the transmission focus 203 may be thereby obtained with good accuracy. Moreover, even if the imaging point locates outside the transmitted sonic wave end 206, the delay amount (D) may be obtained with good accuracy.

The correction operation performed by the correction operation part 610 will be explained with reference to FIG. 4. For example, the delay amount (D) for the imaging point 802 is obtained by using a delay amount ($D_1$) obtained by the virtual sound source method-based delay amount calculation part 609, and a delay amount ($D_2$) obtained by the virtual sound source method for a point 803 obtained by projecting the imaging point 802 on the line of the transmitted sonic wave end 206, or between two of the transmitted sonic wave ends 206. Specifically, the point 803 is a point obtained by projecting the imaging point 802 on the sound axis 702, the transmitted sonic wave end 206, or an arbitrary line preliminarily defined in the region between the transmitted sonic wave ends 206. The imaging point 802 is projected by moving it to a position on such a line as mentioned above along the direction perpendicular to the sound axis 702.

The delay amount ($D_2$) obtained for the point 803 by the virtual sound source method may also be obtained an operation performed by the virtual sound source method-based delay amount calculation part 609, or it may also be obtained by calculation from the value of the delay amount ($D_1$) obtained for the imaging point 802. By calculating the delay amount ($D_2$) from the delay amount ($D_1$), calculation complexity imposed on the receiving beamformer 603 may be reduced. Specifically, when the point 803 is a point on the transmitted sonic wave end 206, the delay amount ($D_2$) is obtained from the value of the delay amount ($D_1$) in accordance with the equation (1).

(Several 1)

$$D_2 = (D_1 |\cos\theta|)/\cos\theta_1 \quad (1)$$

$\theta_1$ is the angle formed by the transmitted sonic wave end 206 and the sound axis 702, and $\theta$ is the angle formed by a line connecting the imaging point and the transmission focus 203, and the sound axis 702.

The correction operation part 610 obtains a corrected delay amount D of the imaging point 802 by weighting the delay amount $D_1$ obtained for the imaging point 802 by the virtual sound source method, and the delay amount ($D_2$) obtained for the point 803 by the virtual sound source method, and adding them, as shown by the equation (2).

[Equation 2]

$$D = \frac{1}{a}D_1 + \frac{a-1}{a}D_2 \quad (2)$$

In the equation (2), a is a weight value, and is obtained in accordance with the following equations (3).

[Equation 3]

$$a = \left(\frac{a_0 - 1}{1 - \sin\theta_1}\right)\sin\theta + \left(a_0 - \frac{a_0 - 1}{1 - \sin\theta_1}\right) \quad (3)$$

Figure 7:
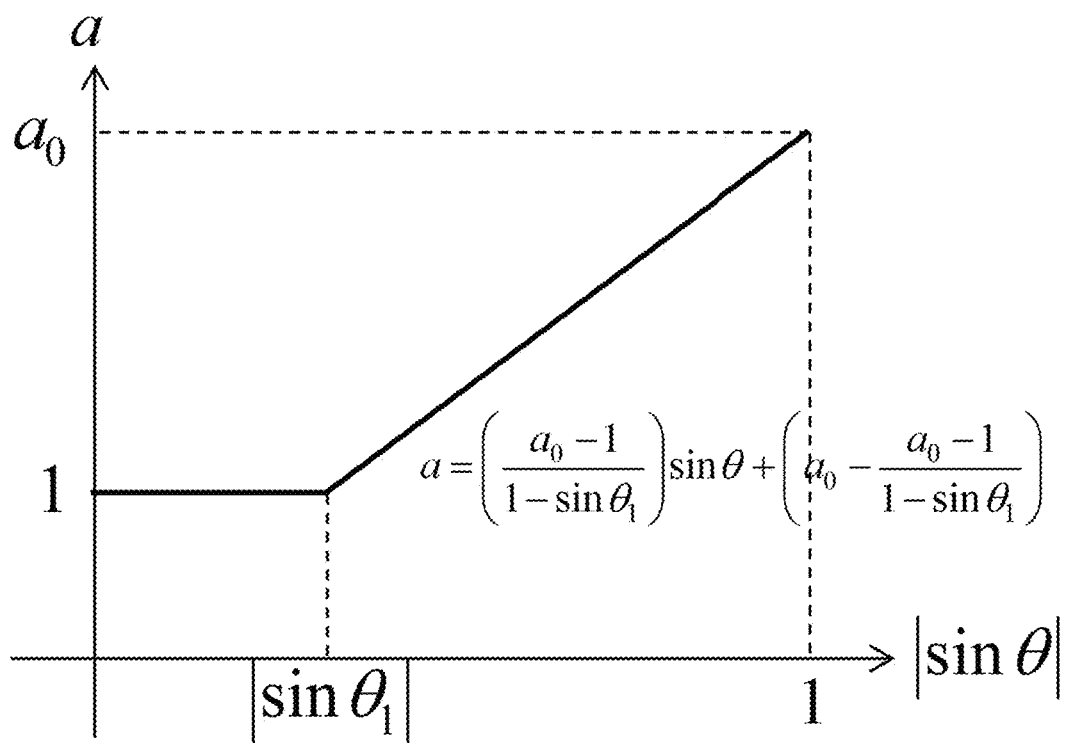
FIG. 7 is a graph showing a function of the weight value a of the first embodiment.

As shown by the equation (3), the weight value a is a function of the variable $\sin\theta$, and such a weight value as drawn in the graph of FIG. 7 is used in this explanation. When the absolute value of $\sin\theta$ is smaller than the absolute value of $\sin\theta_1$, the imaging point 802*a* is in the region between the transmitted sonic wave ends 206 as shown in FIG. 4. Therefore, a is set to be 1, thus the weight for $D_2$ ((a−1)/a) mentioned in the equation (2) is 0, and the delay amount D is equal to $D_1$. That is, when the imaging point 802*a* is in the region between the transmitted sonic wave ends 206, the delay amount (D) is equal to the delay amount ($D_1$) obtained by the virtual sound source method-based delay amount calculation part 609.

When the absolute value of $\sin\theta$ is 1, the imaging point 802*c* is at a position on the same horizontal level as that of the transmission focus 203. In such a case, $a_0$ is set as a ($a_0$ is a constant larger than 1) as shown in FIG. 7, and the delay amount D is set so that, in the right-hand side of the equation (2), the weight of $D_2$ of the second member ((a−1)/a) is larger than the weight of $D_1$ of the first member (1/a).

When the absolute value of $\sin\theta$ is not smaller than the absolute value of $\sin\theta_1$ and smaller than 1, a is set to be a value larger than 1 and smaller than $a_0$ depending on the value of $\sin\theta$ as shown in FIG. 7, and in the right-hand side of the equation (2) representing the delay amount D, the weight of $D_2$ of the second member is larger than that of the case where the absolute value of $\sin\theta$ is the same as the absolute value of $\sin\theta_1$, and the weight of $D_2$ is smaller than that of the case where the absolute value of $\sin\theta$ is 1.

Figure 8:
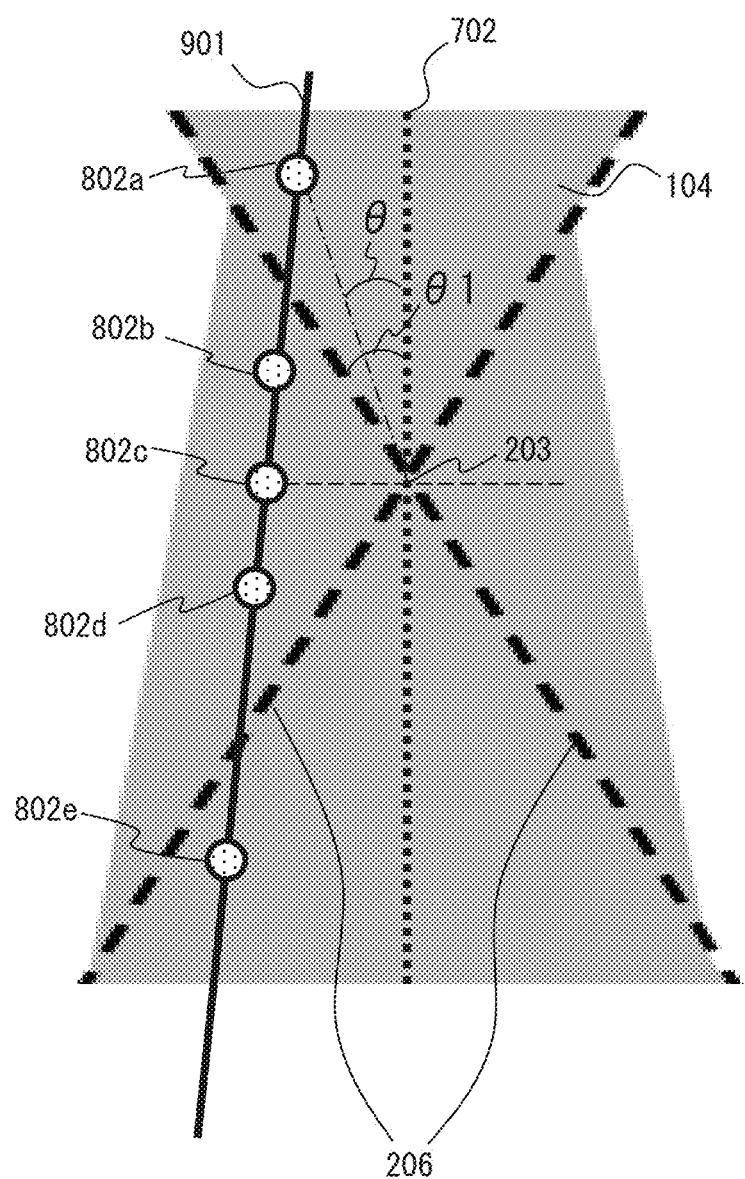
FIG. 8 is a drawing for explaining the principle of obtaining corrected delay amounts for imaging points on a scanning line 901 in the first embodiment

Thus, for the imaging points 802*a* and 802*e* locating within the region between the transmitted sonic wave ends 206 among the imaging points locating on the scanning line 901 as shown in FIG. 8, the delay amount ($D_1$) obtained by the virtual sound source method is set. For the imaging points 802*b*, 802*c*, and 802*d* locating outside the region between the transmitted sonic wave ends 206, a delay amount (D) determined according to the angle $\theta$ formed by the line connecting each of these points and the transmitting focus 203, and the sound axis 702 is set. Accordingly, the delay amount (D) can be obtained with good accuracy even for an imaging point locating near the transmission focus 203, or outside the region between the transmitted sonic wave ends 206.

Operation of the whole receiving beamformer 603 mentioned above is explained with reference to FIG. 9. The receiving beamformer 603 is constituted by, for example, CPU and a memory storing programs, and CPU reads and executes the programs to realize the operations of the virtual sound source method-based delay amount calculation part 609 and the correction operation part 610.

Figure 9:
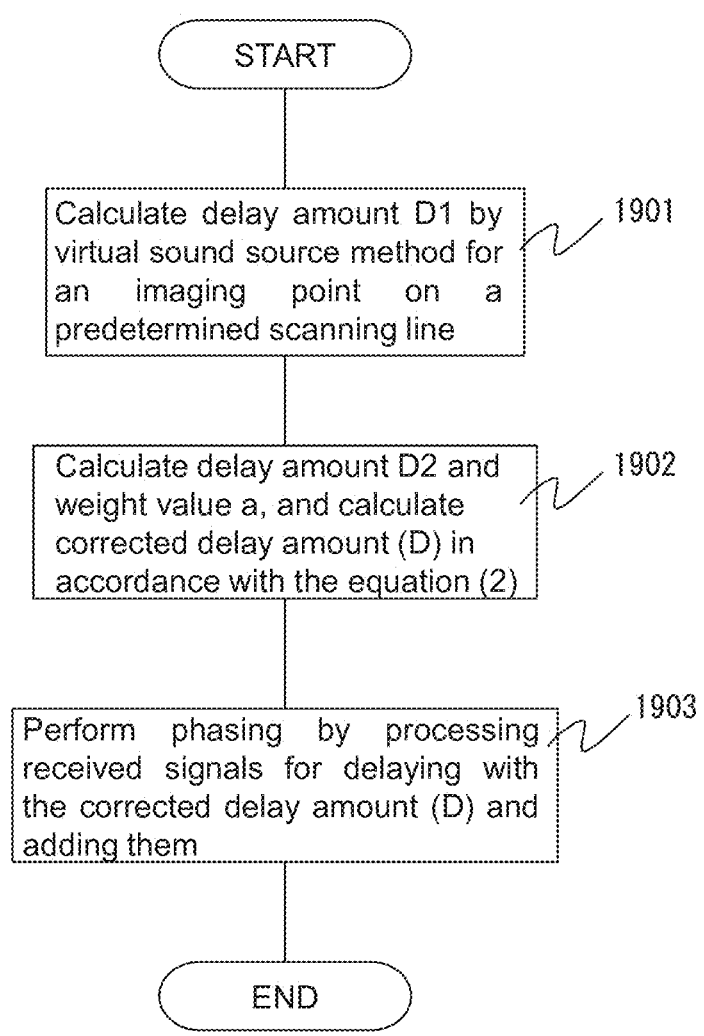
FIG. 9 is a flowchart showing operation of the receiving beamformer of the first embodiment.

First, in the step 1901 shown in FIG. 9, the virtual sound source method-based delay amount calculation part 609 of the receiving beamformer 603 receives the position of the transmission focus from the transmitting beamformer 602, and receives the position of the scanning line 901 from the control part 606. The delay amount ($D_1$) is calculated by the virtual sound source method for each of a plurality of imaging points defined on the scanning line 901 with a predetermined interval.

Then, in the step 1902, the correction operation part 610 obtains the delay amount ($D_2$) for a point obtained by projecting each imaging point on the transmitted sonic wave end 206 from the delay amount ($D_1$) for each imaging point obtained in the step 1901 in accordance with the equation (1) mentioned above. As $\theta_1$ contained in the equation (1), a value obtained by an operation from depth of the transmission focus 203 received from the transmitting beamformer 602 and the positions of the both ends of the driven ultrasonic elements 600 is used. Alternatively, a value obtained beforehand for each depth of the transmission focus 203 may also be used as $\theta_1$. As $\theta$, a value obtained by an operation from the positions of the imaging point on the scanning line 901 and the transmission focus 203 is used. Alternatively, a value obtained beforehand for every combination of each imaging point and the transmission focus 203 may be used as $\theta$. Furthermore, the correction operation part 610 substitutes such values as mentioned above for $\theta_1$ and $\theta$ in the equation (3) to obtain weight value a for each imaging point. The obtained values of a, $D_2$, and the delay amount $D_1$ obtained in the step 1901 are substituted for those of the equation (2) to calculate the corrected delay amount (D).

The process advances to the step 1903, and the correction operation part 610 receives signals received by each ultrasonic element 600 via the transmission/reception separation circuit (T/R) 604, and performs phasing of them by delaying them by the corrected delay amount (D), and adding them. By performing this operation for each imaging point on the scanning line 901, phasing of the received signals is carried out for every imaging point on the scanning line 901 to generate an image of one raster (phased output), and it is delivered to the image processing part 605.

The image processing part 605 performs processings for putting the phased outputs (rasters) of a plurality of scanning lines 901 in order etc. to generate an ultrasonogram, and displays it on the image display part 607.

As described above, according to the present invention, there may be obtained a delay amount (D) by correcting the delay amount ($D_1$) obtained by the virtual sound source method. Since the delay amount (D) may be obtained with good accuracy irrespective of whether the imaging point locates within the main lobe or not, sufficiently accurate phased output (raster) is obtained even for the scanning line 901 at a position remote from the transmission focus 203. Therefore, the area in which the scanning line 901 can be set is wide, and a plurality of phased outputs (rasters) for a wide area are generated by one time of transmission. A highly precise image is thereby generated with a small number of times of transmission.

Although FIG. 7 shows an example where the function of a is a function representing a straight line connecting the point of sin θ=1 and a=$a_0$, and the point of sin θ=|sin $θ_1$| and a=1, this embodiment is not limited to the function shown in FIG. 7. It may be a function representing an arbitrary curve connecting the point of sin θ=1 and a=$a_0$, and the point of sin θ=|sin $Ω_1$| and a=1.

Although the weight value a is set on the basis of the angle θ in the aforementioned embodiment, there may also be employed a configuration that the weight value a is set on the basis of the distance from the transmission focus 203 to the imaging point 802, or the like, or on the basis of both the angle θ and the distance.

Further, although the method of moving the imaging point 802 along the direction perpendicular to the sound axis is explained as the projection method for obtaining the point 803, for which the delay amount $D_2$ is obtained, the method is not limited to this method. It is of course also possible to obtain a point 803 of at a position on a shape further closer to the actual wave face, and obtain the delay amount $D_2$ for such a point 803.

Second Embodiment

The ultrasonic imaging apparatus of the second embodiment of the present invention will be explained with reference to FIG. 10.

Figure 10:
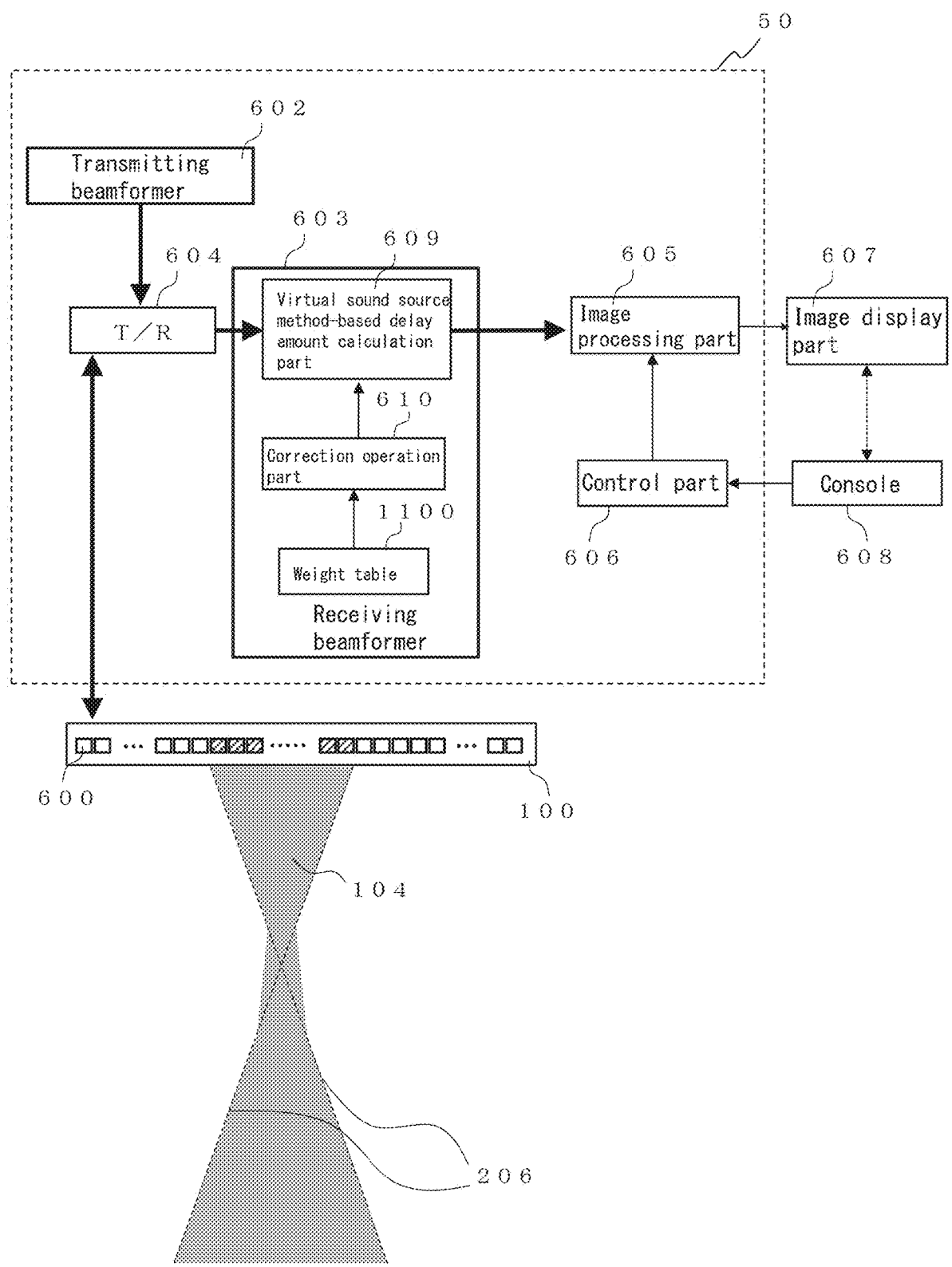
FIG. 10 is a block diagram showing the configuration of the ultrasonic diagnostic apparatus of the second embodiment.

As shown in FIG. 10, the ultrasonic imaging apparatus of the second embodiment has the same configurations as those of the ultrasonic diagnostic apparatus of the first embodiment (FIG. 3), but a storage part that stores weight values for every imaging position (weight table 1100) is further provided in the correction operation part 610. In the weight table 1100, weight values a obtained beforehand for all the combinations of the imaging points and transmission focus 203 that can be set are stored. Since the weight value a is a function of the angle θ formed by the line connecting the imaging point and the transmission focus, and the optical axis, as explained for the first embodiment with reference to the equation (3), it may be obtained beforehand for each of combinations of supposed imaging points and transmission focus.

Thus, the correction operation part 610 may read a weight value from the weight table 1100, and used it in the step 1902 shown in FIG. 9. Therefore, it is not necessary to calculate the weight value for every imaging, and the computational complexity imposed on the correction operation part 610 can be reduced. Improvement in the operation speed and smaller size of the receiving beamformer 603, as well as lower cost of the ultrasonic imaging apparatus can be thereby realized.

The configurations and operation of the apparatus of this embodiment other than those explained above are the same as those of the first embodiment, and therefore explanations thereof are omitted.

Third Embodiment

The ultrasonic imaging apparatus of the third embodiment of the present invention will be explained with reference to FIG. 11.

Figure 11:
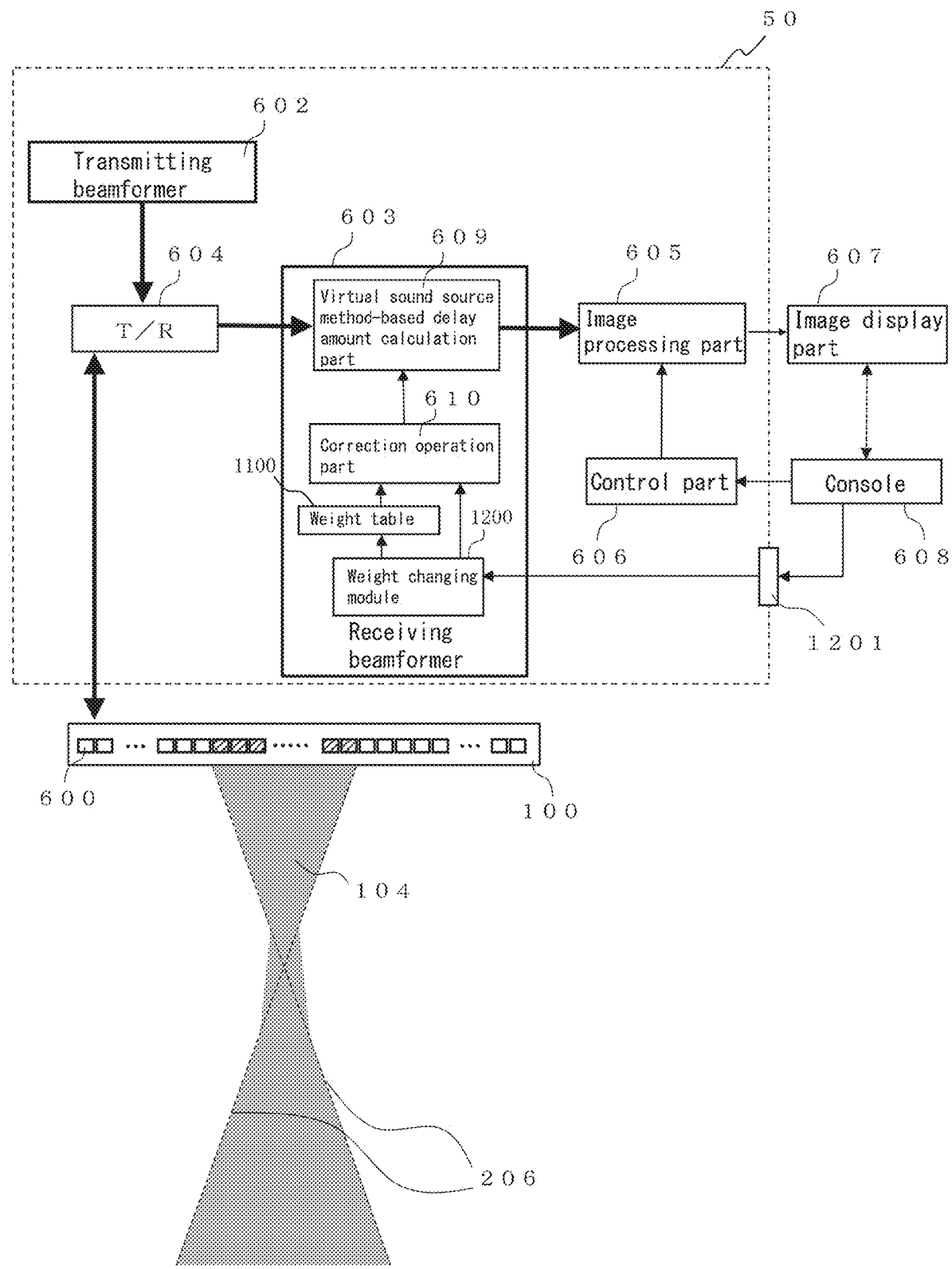
FIG. 11 is a block diagram showing the configuration of the ultrasonic diagnostic apparatus of the third embodiment.

Although the ultrasonic imaging apparatus of the third embodiment has the same configurations as those of the ultrasonic imaging apparatus of the second embodiment (FIG. 10), a weight changing module 1200 is further disposed in the receiving beamformer 603 as shown in FIG. 11. According to this embodiment, the console 608 functions also as a reception part that receives the weight value a inputted by an operator. Specifically, the weight changing module 1200 is connected to the console 608 through an input/output port 1201 provided on a main body 50 of the ultrasonic imaging apparatus.

The weight changing module 1200 receives each value for weight value a, or the values for the whole table from the operator through the console 608, and substitutes them for values or table stored in the weight table 1100. The weight values a may be thereby changed to appropriate values depending on characteristics of a subject to be imaged, and therefore a delay amount (D) suitable for the subject may be obtained with the correction operation part 610. Since the other configurations and operation are the same as those of the second embodiment, explanations thereof are omitted.

Further, the weight changing module 1200 may also be provided in the receiving beamformer 603 that is not provided with the weight table 1100. In this case, the weight changing module 1200 changes value of a parameter to be used for the calculation of the weight value a by the correction operation part 610 to a value received via the console 608. For example, it changes value of the constant $a_0$ to be used for the operation of the equation (3) to a value received via the console 608. Since the value of $a_0$ may be thereby changed depending on subject to a value suitable for the subject, a delay amount (D) suitable for the subject can be obtained by the correction operation part 610.

Since other configurations and operation are the same as those of the first and second embodiments, explanations thereof are omitted.

Fourth Embodiment

Figure 12:
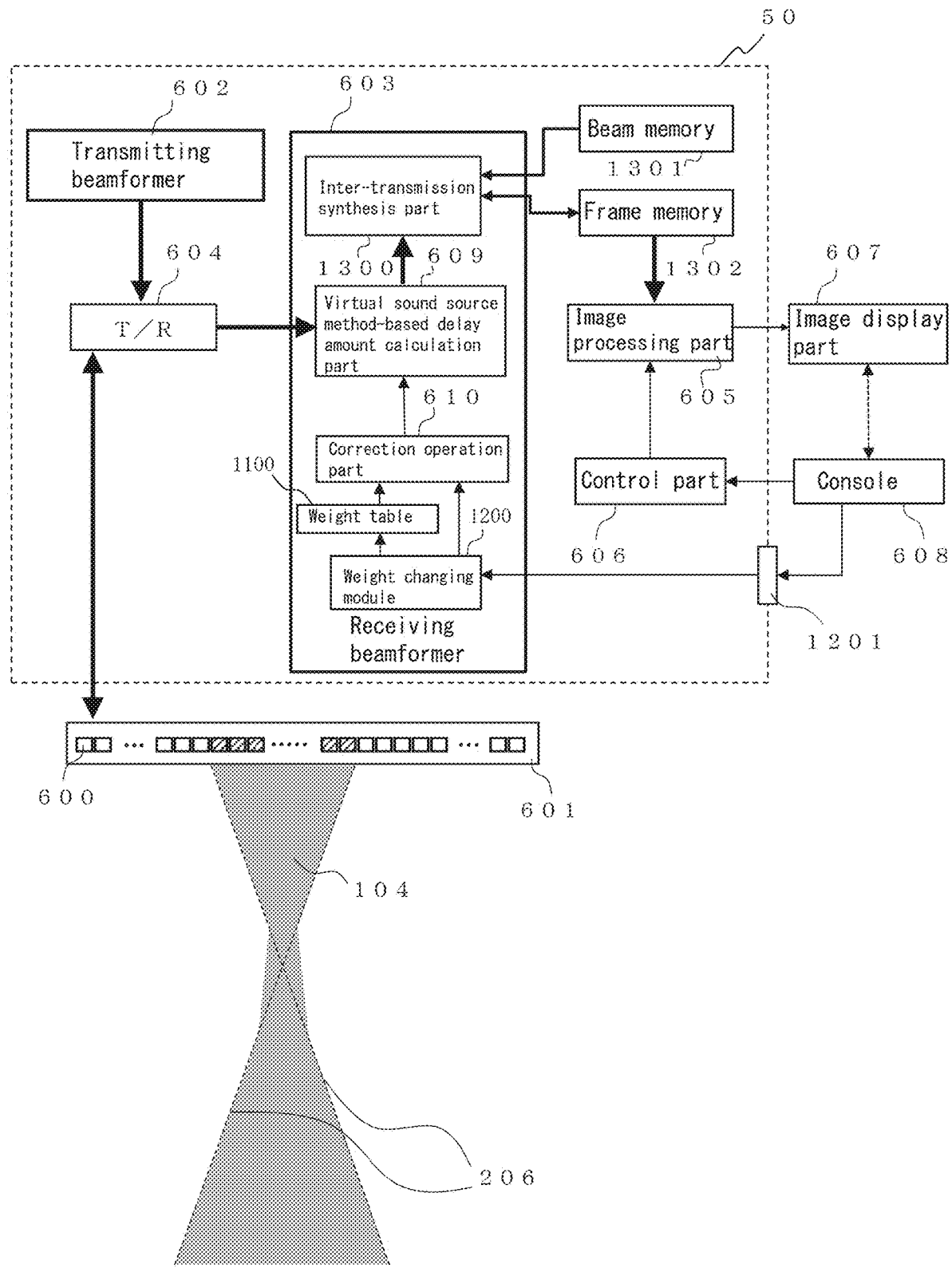
FIG. 12 is a block diagram showing the configuration of the ultrasonic diagnostic apparatus of the fourth embodiment.

The ultrasonic imaging apparatus of the fourth embodiment of the present invention will be explained with reference to FIG. 12.

The receiving beamformer 603 of the ultrasonic imaging apparatus of the fourth embodiment performs beamforming according to the aperture synthesis method. As shown in FIG. 12, the apparatus further comprises a phased output storage part (beam memory 1301) that stores phased output of the receiving beamformer 603. The receiving beamformer 603 reads out a phased output obtained from a received signal of the ultrasonic beam 104 of a certain transmission from the phased output storage part, and synthesizes it with a phased output obtained from a received signal of the ultrasonic beam of another transmission. The above will be further explained.

In the receiving beamformer 603, an inter-transmission synthesis part 1300 is disposed, and in the main body 50, a frame memory 1302 is also disposed besides the beam memory 1301. The other configurations are the same as those of the third embodiment.

Figure 13:
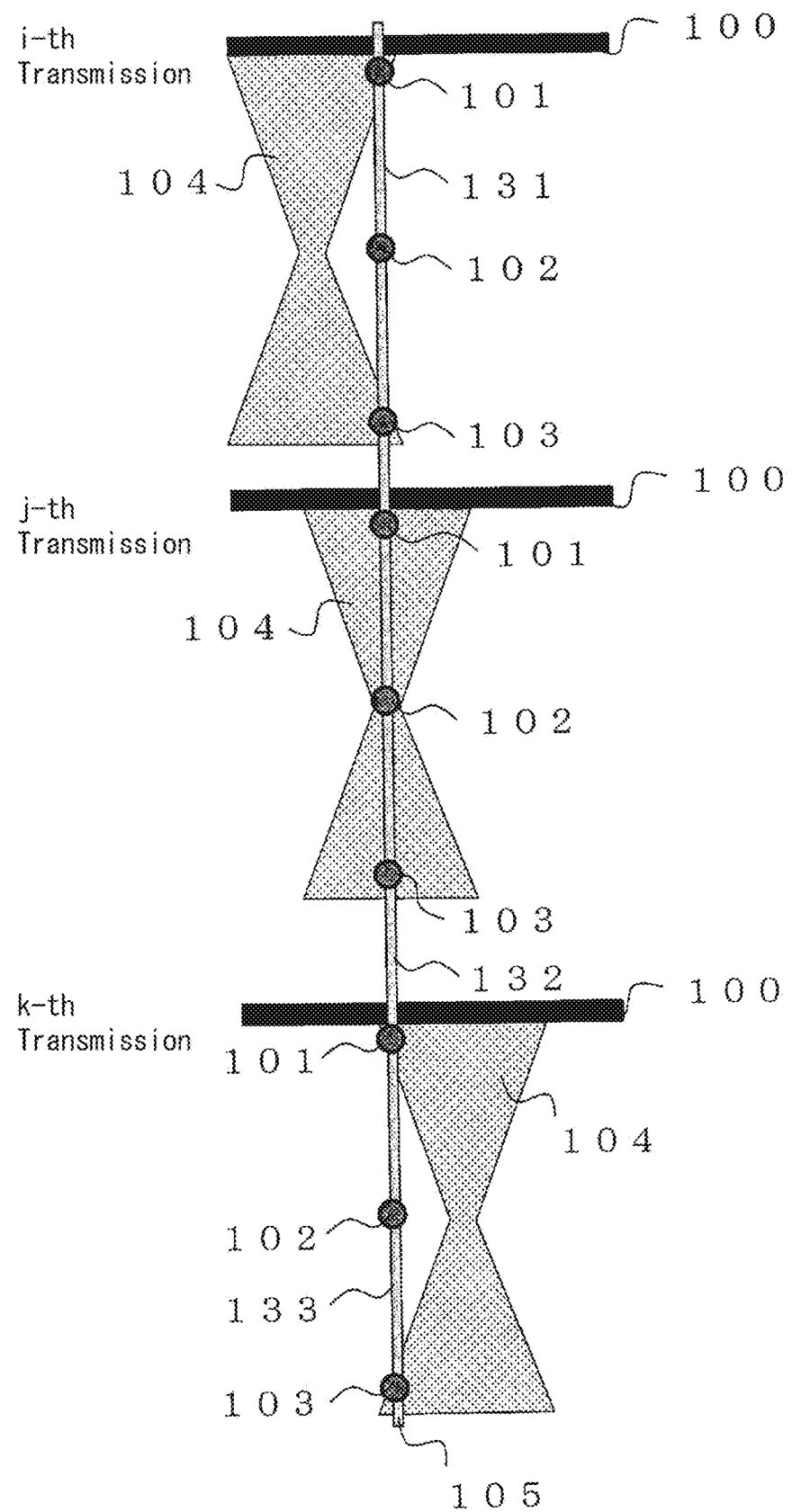
FIG. 13 is a drawing for explaining the aperture synthesis processing performed by the inter-transmission synthesis part 1300 of the fourth embodiment.

The receiving beamformer 603 sets a plurality of scanning lines for each transmission, and carries out phasing addition of the received signals for a plurality of imaging points on each scanning line by using the delay amounts (D) obtained by the virtual sound source method-based delay amount calculation part 609 and the correction operation part 610. Phased outputs (rasters) are thereby obtained. A plurality of the obtained phasing outputs (rasters) are sent to the beam memory 1301 via the inter-transmission synthesis part 1300 and stored therein. The inter-transmission synthesis part 1300 reads out a plurality of phased results for a specific (the same) imaging point from a plurality of phased outputs (rasters) stored in the beam memory 1301, and synthesizes them (aperture synthesis). For example, as shown in FIG. 13, when phased outputs obtained by i-th transmission and j-th transmission for scanning lines 131 and 132 at the same positions as that of a scanning line 133, for which phased outputs are obtained by the k-th transmission, are stored in the beam memory 1301, the inter-transmission synthesis part 1300 reads out the phased outputs of the i-th transmission and the j-th transmission for an imaging point 101 from the beam memory 1301, and synthesizes them with the phased output of the imaging point 101 of the k-th transmission (aperture synthesis). Similarly, phased outputs are synthesized for every imaging point such as the other imaging points 102 and 103. By performing the aperture synthesis as described above, accuracy of the phased outputs for each imaging point can be enhanced.

The aperture synthesis image obtained from the synthesis processing is stored in the frame memory 1302, sent to the image processing part 605, and displayed on the image display part 607. The image processing part 605 displays the image obtained by the aperture synthesis on the image display part 607.

Since the other configurations and operation such as those of the weight changing module 1200 are the same as those of the third embodiment and the first embodiment, explanations thereof are omitted.

Since the receiving beamformer 603 of the present invention correct the delay amount ($D_1$) obtained by the virtual sound source method to obtain the corrected delay amount (D), a phased output (raster) is obtained with good accuracy even for an imaging point at a position remote from the transmission focus 203 (scanning line 901), irrespective of whether the imaging point is inside the main beam or not. Therefore, a plurality of rasters are obtained for a wide area with one time of transmission. Accordingly, by storing them in the beam memory 1301, and carrying out the aperture synthesis with rasters obtained by another transmission, rasters of higher accuracy are generated, and used to generate an image.

Fifth Embodiment

The ultrasonic imaging apparatus of the fifth embodiment of the present invention will be explained with reference to FIGS. 14 to 16. The receiving beamformer 603 of the ultrasonic imaging apparatus of the fifth embodiment performs high frame rate imaging and beamforming by the aperture synthesis method.

Figure 14:
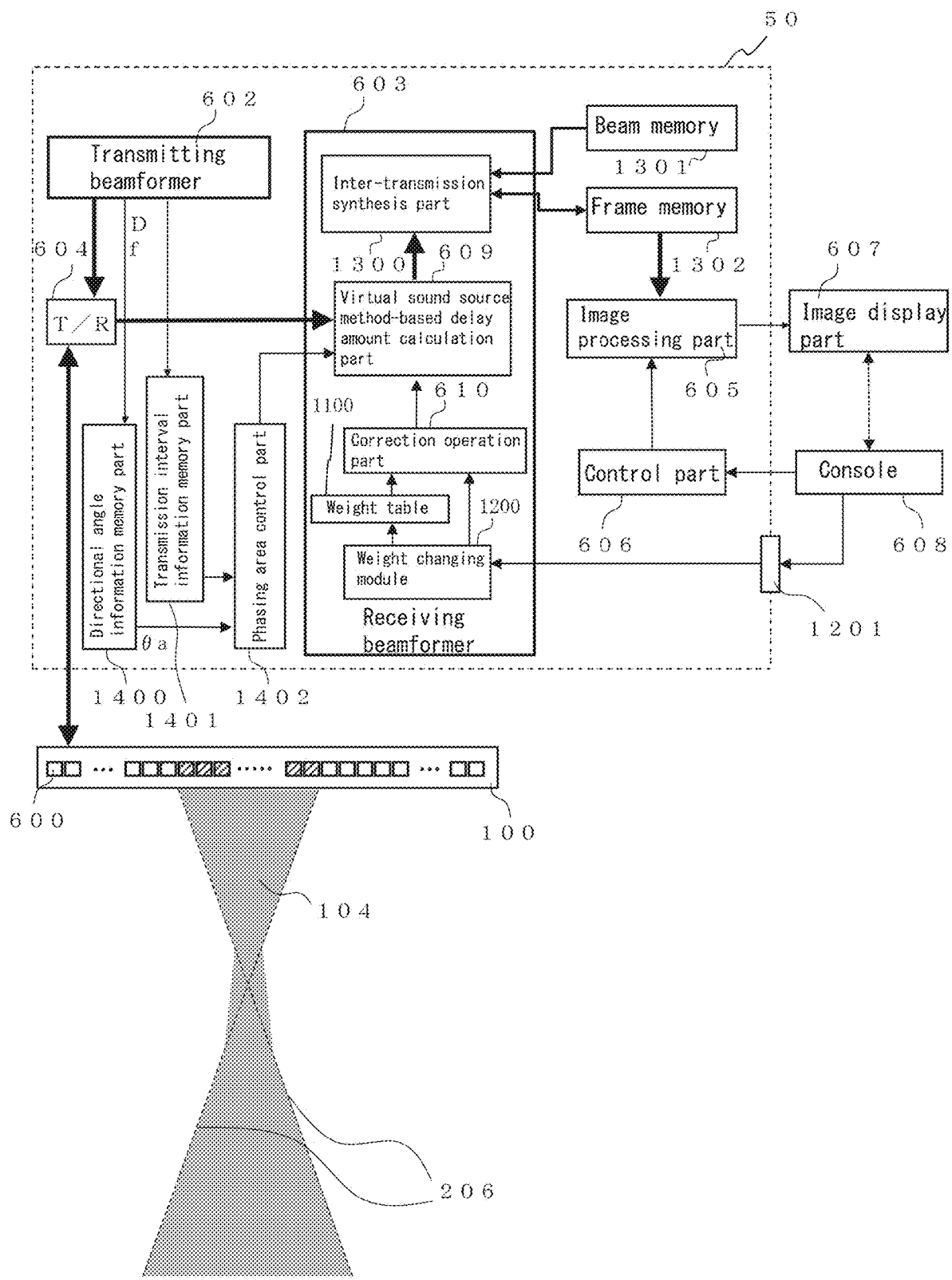
FIG. 14 is a block diagram showing the configuration of the ultrasonic diagnostic apparatus of the fifth embodiment.

As shown in FIG. 14, a phasing area control part 1402 that defines an area of imaging points for which the receiving beamformer 603 performs phasing processing is further provided in the main body 50. The phasing area control part 1402 defines the phasing area by using an angle range larger than the transmission directional angle at the time of transmission of the ultrasonic beam 104 by the transmitting beamformer 602, and two lines of the transmitted sonic wave ends 206. In the main body 50, a directional angle information memory part 1400 and a transmission interval information memory part 1401 are further provided. Since the other configurations are the same as those of the ultrasonic imaging apparatus of the fourth embodiment, explanations thereof are omitted.

The directional angle information memory part 1400 receives transmission aperture P and transmission frequency f among the set parameters from the transmitting beamformer 602, obtains transmission directional angle $\theta_a$ by calculation in accordance with the equation (4), and memorizes it.

[Equation 4]

$$\sin \theta_a = v/(f \cdot P) \quad (4)$$

The symbol v represents acoustic velocity in a subject, and it is supposed that oscillators of the ultrasonic elements 600 have a rectangular shape.

The transmission interval information memory part 1401 receives information on transmission interval of the transmission beam (ultrasonic beam) 104 in the direction along the probe array 100 from the transmitting beamformer 602, and memorizes it. The phasing area control part 1402 receives the transmission directional angle $\theta_a$ and the transmission interval 503b from the directional angle information memory part 1400 and the transmission interval information memory part 1401, respectively, determines a phasing area 105b that defines area of imaging points on the basis of them, and specifies it for the virtual sound source method-based delay amount calculation part 609. The virtual sound source method-based delay amount calculation part 609 calculates delay amounts for imaging points in the specified phasing area 105b.

The operation of the phasing area control part 1402 will be further explained with reference to FIGS. 15, (a) and (b). The phasing area 105b may generally be obtained by a simple transmission sound field drawing method. In the case of the convergence transmission in which transmission beam is focused with an electronic focus, acoustic lens, concave surface oscillator, etc., intersecting lines (transmitted sonic wave ends) 206 crossing at the transmission focus 203 are first drawn from the ultrasonic elements 602 at the both ends of the transmission caliber, as shown in FIG. 15, (a). Then, two lines 207a forming a transmission directional angle $\theta_a$ are drawn on both sides of the transmission sound axis 702. The area enclosed by the outside lines among the transmitted sonic wave ends 206 and the lines 207a is a general phasing area 105a.

Figure 15:
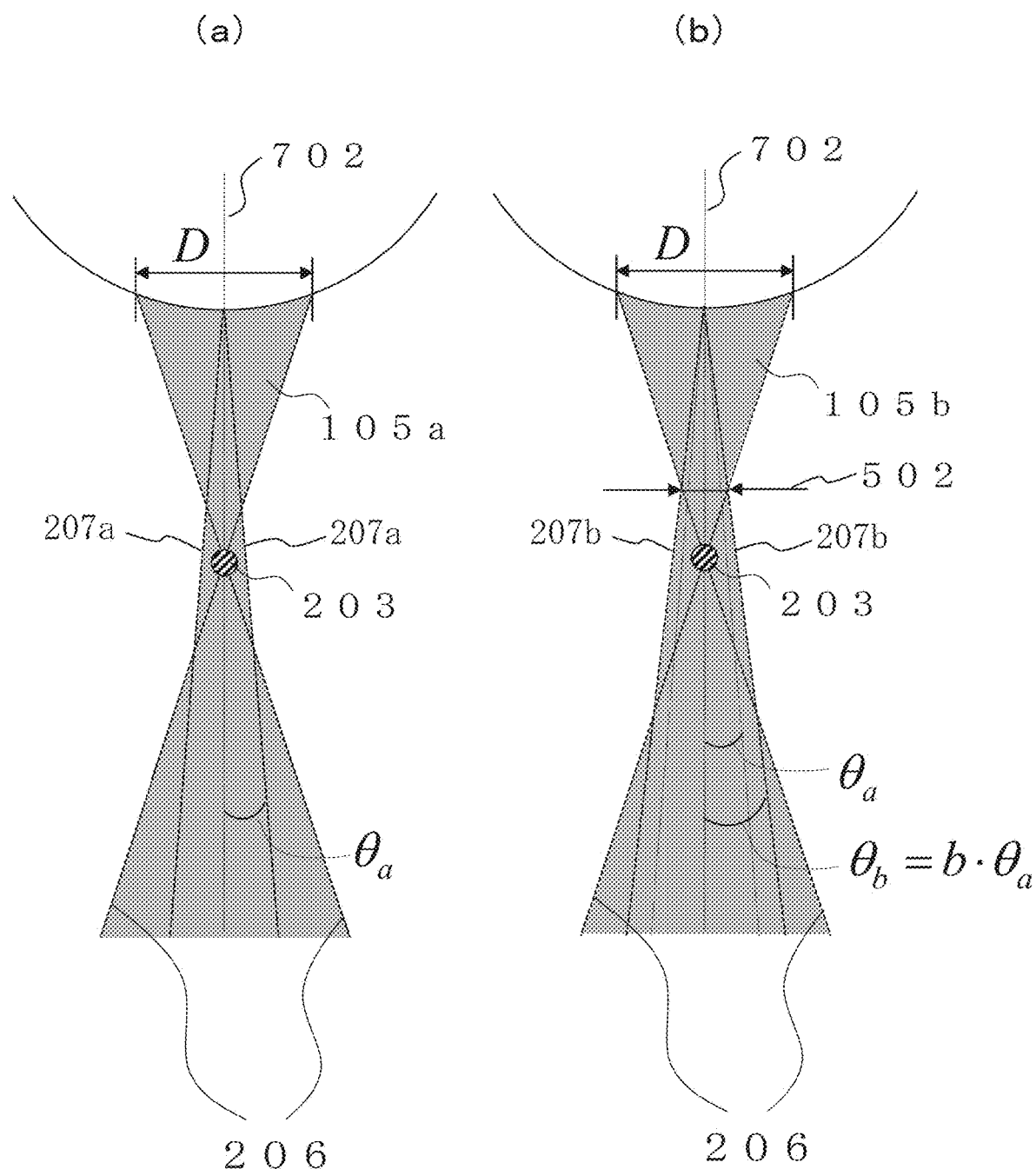
FIG. 15, (a) is an explanatory drawing showing the phasing area 105a of the conventional ultrasonic diagnostic apparatus.

According to this embodiment, as shown in FIG. 15, (b), the phasing area control part 1402 draws two lines 207b using the value of transmission directional angle $\theta_b$ obtained by multiplying the transmission directional angle $\theta_a$ by a coefficient b as shown by the equation (5). The area enclosed by the outside lines among the transmitted sonic wave ends 206 and the lines 207b is set to be the phasing area 105b.

[Equation 5]

$$\theta_b = b \cdot \theta_a \quad (5)$$

Figure 16:
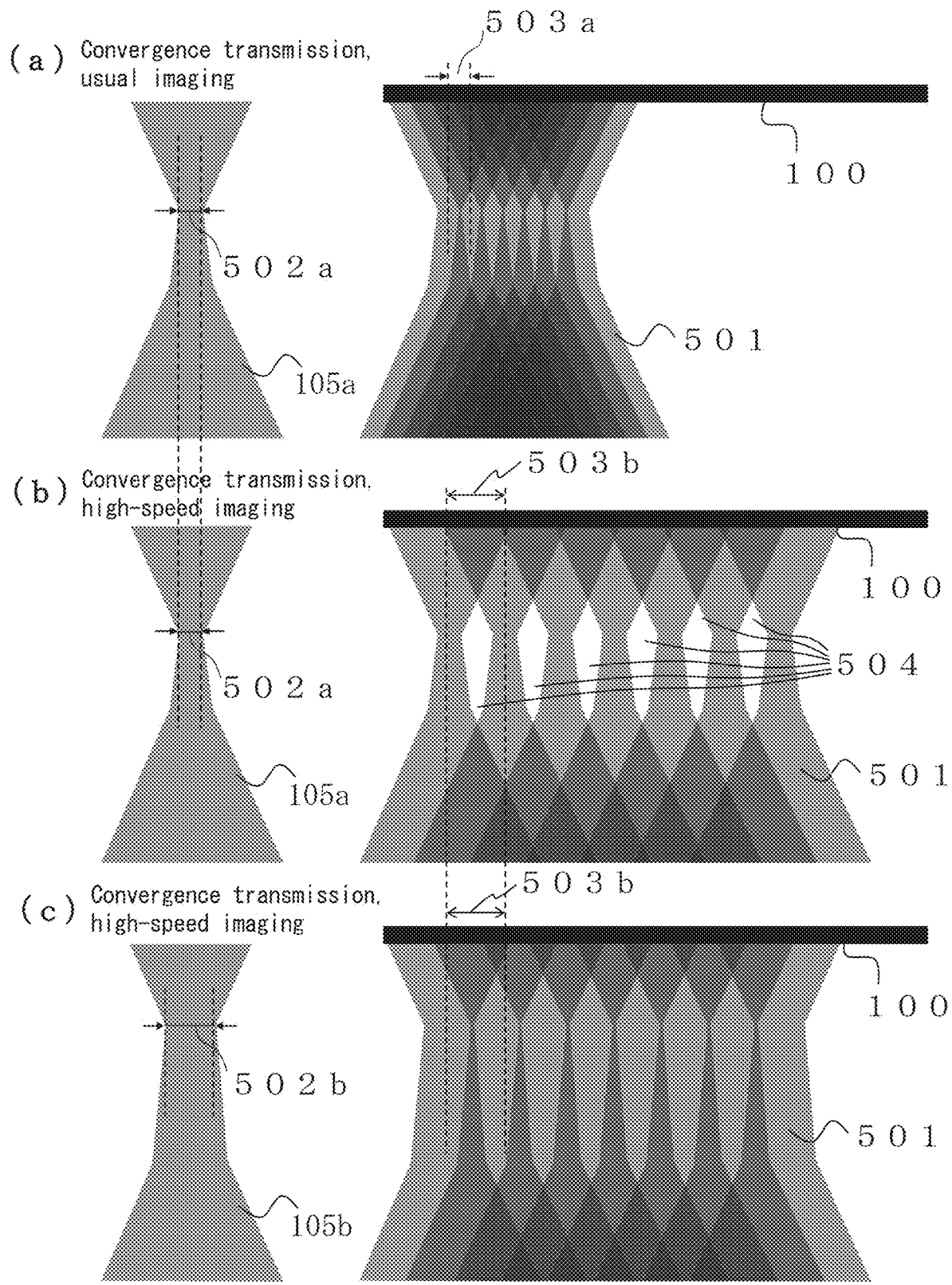
FIG. 16, (a) is an explanatory drawing showing the phasing area 105a and an image generation area 501 of the conventional usual imaging.

The coefficient b is set by the phasing area control part 1402 with reference to an equation or table defined beforehand so that the minimum width 502b of the phasing area 105b becomes larger than the transmission interval 503b read from the transmission interval information memory part 1401, as shown in FIG. 16, (c).

Since the receiving beamformer 603 of the present invention obtains the corrected delay amount (D) by correcting the delay amount ($D_1$) obtained by the virtual sound source method, it obtains the delay amount (D) with good accuracy even for an imaging point at a position remote from the transmission focus 203. Therefore, phased output (raster) is obtained with good accuracy by using the corrected delay amount (D).

By extending the phasing area 105b as shown in FIG. 16, (c), there may be set the transmission interval 503b, which cannot be set with the usual phasing area 105a, because, with such a usual phasing area, the phasing areas 105a of the minimum width 502a do not overlap with each other, and there remain omission regions 504, as shown in FIG. 16, (b). Therefore, as shown in FIG. 16, (c), by setting a transmission interval 503b larger than the transmission interval 503a required when the conventional phasing area 105a is used as shown in FIG. 16, (a), high frame rate imaging (high speed imaging) can be performed.

Since a plurality of rasters in a wide area may be obtained by one time of transmission by extending the phasing area 105b, by storing these in the beam memory 1301, and performing the aperture synthesis with them together with rasters obtained by other transmissions, an ultrasonogram of high precision can be generated for an area 501 (FIG. 16, (c)).

If the overlapping areas of the phasing areas 105b of a plurality of times of transmissions are small, block noises are generated in an image obtained after the aperture synthesis. Therefore, it is preferable to set the coefficient b so that the phasing areas 105b of at least three or more times of transmissions overlap with each other.

Since the other configurations and operation are the same as those of the fourth embodiment, explanations thereof are omitted.

Sixth Embodiment

Figure 17:
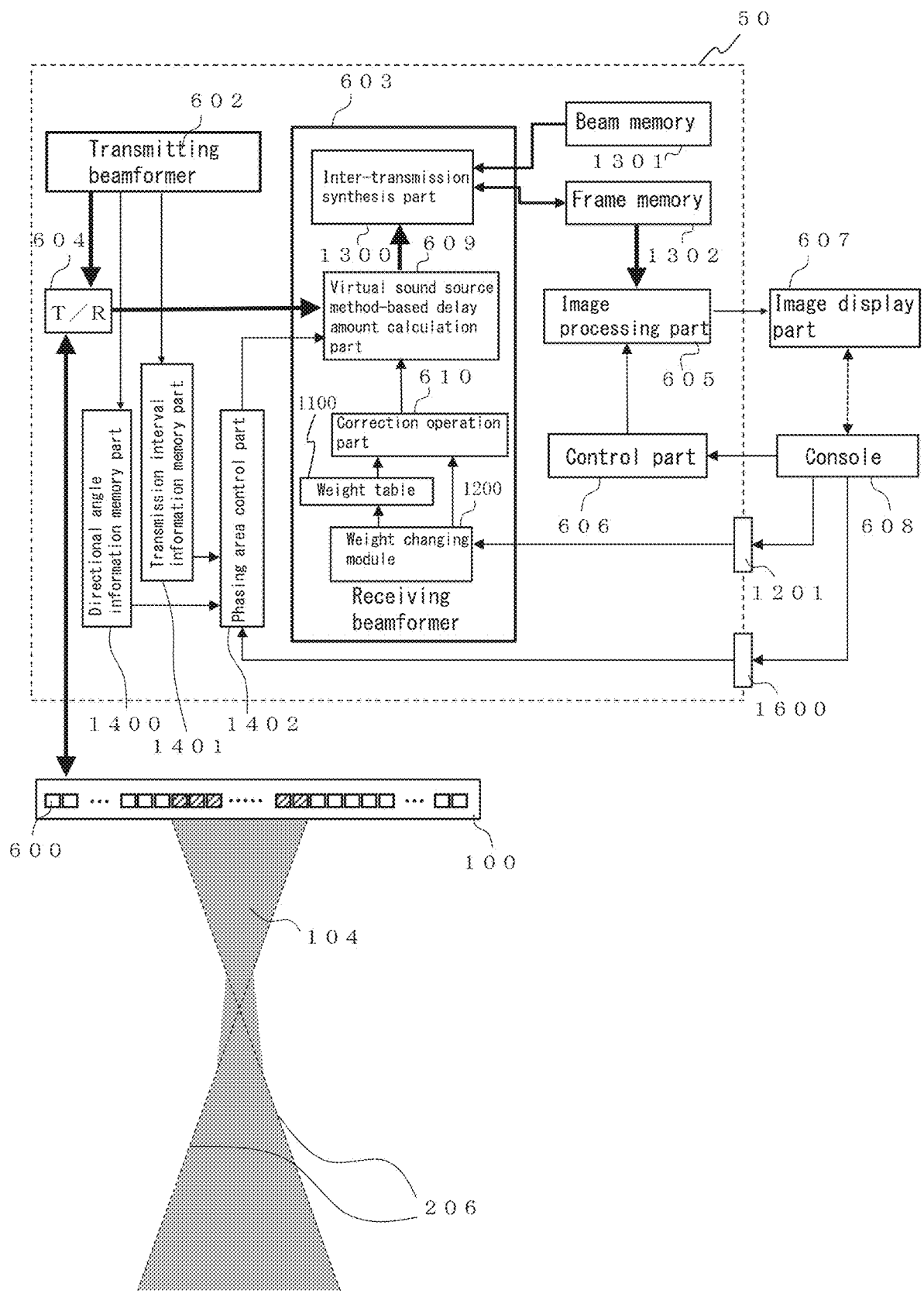
FIG. 17 is a block diagram showing the configuration of the ultrasonic diagnostic apparatus of the sixth embodiment.

The ultrasonic imaging apparatus of the sixth embodiment of the present invention will be explained with reference to FIG. 17. Although the ultrasonic imaging apparatus of the sixth embodiment has the same configurations as those of the ultrasonic imaging apparatus of the fifth embodiment (FIG. 14) as shown in FIG. 17, it is configured so that the phasing area control part 1402 may be adjusted from the outside. Specifically, the console 608 functions also as a reception part that receives a coefficient used for processing of the phasing area control part 1402. An input-and-output port 1600 is disposed in the main body 50, and the phasing area control part 1402 is connected to the console 608. The phasing area control part 1402 obtains an angle range ($θ_b$) by multiplying the transmission directional angle $θ_a$ by the coefficient received by the reception part (console 608).

The operator manually sets the value of the coefficient b of the equation (5) explained for the fifth embodiment, or finely tuning the coefficient b set by the phasing area control part 1402, by using the console 608.

The value of the coefficient b is thereby appropriately adjusted according to scattering state of sonic waves, which varies depending on subjects, and therefore an appropriate phasing area 105b can be set. Accordingly, even by high frame rate imaging, an ultrasonogram of higher precision can be generated.

DESCRIPTION OF NUMERICAL NOTATIONS

100 Probe array
104 Transmission beam (ultrasonic beam)
105a and 105b Phasing area
202 Transmission caliber center point
203 Transmission focus
206 Transmitted sonic wave end
501 Phasing area of aperture synthesis for a plurality of times of transmission
503a and 503b Transmission interval
504 Omission region where phasing areas do not overlap
609 Virtual sound source method-based delay amount calculation part
610 Correction operation part
700 Transmitted sonic wave face at transmission focus depth
901 Virtual scanning line
1100 Weight table

The invention claimed is:

1. An ultrasonic imaging apparatus, comprising:
an ultrasonic element array in which a plurality of ultrasonic elements are arranged along a predetermined direction;
a transmitting beamformer that forms an ultrasonic beam to be transmitted into a subject by the ultrasonic element array;
a computer coupled to the ultrasonic element array and the transmitting beamformer; and
a controller coupled to the computer that generates image data using results outputted by a receiving beamformer,
wherein the transmitting beamformer performs convergence transmission that forms a transmission focus of the ultrasonic beam in the subject, and
wherein the computer is programmed to:
perform phasing of a plurality of received signals obtained by receiving the ultrasonic waves reflected in the subject with the ultrasonic element array by delaying received signals,
obtain delay amounts of the received signals based on the transmission focus as a virtual sound source, and
correct the obtained delay amounts based on positions of an imaging point,
wherein, the imaging point is outside a transmitted sonic wave region bound by two virtual lines projecting from different ultrasonic elements of the ultrasound element array and through the transmission focus,
wherein the computer is further programmed to:
correct a first delay amount ($D_1$) obtained for the imaging point using a second delay amount ($D_2$) obtained for a point located on one of the two virtual lines of the transmitted sonic wave region,
wherein the point located on one of the two virtual lines of the transmitted sonic wave region is a projection of the imaging point in a direction perpendicular to a sound axis of the ultrasonic beam.

2. The ultrasonic imaging apparatus according to claim 1, wherein computer is further programed to:
obtain the second delay amount ($D_2$) by an operation using the first delay amount ($D_1$), and an angle θ formed by a line connecting the imaging point and the transmission focus, and a sound axis of the ultrasonic beam.

3. The ultrasonic imaging apparatus according to claim 1, wherein the computer is further programed to: weight the first delay amount ($D_1$) and the second delay amount ($D_2$) with weight values and to add the first delay amount ($D_1$) and the second delay amount ($D_2$).

4. The ultrasonic imaging apparatus according to claim 3, wherein the weight values used for the weighting vary depending on an angle θ formed by a virtual line connecting the imaging point and the transmission focus, and a sound axis of the ultrasonic beam.

5. The ultrasonic imaging apparatus according to claim 3, wherein the computer is programmed to receive input of the weight values.

6. The ultrasonic imaging apparatus according to claim 1, wherein the computer is programmed to:
store phased outputs, and
determine a phased output obtained from a received signal of the ultrasonic beam of a certain transmission, and synthesizes it with a phased output obtained from a received signal of the ultrasonic beam of another transmission.

* * * * *